United States Patent [19]

Salim

[11] Patent Number: 4,959,369

[45] Date of Patent: Sep. 25, 1990

[54] SYNERGISTIC COMBINATIONS

[76] Inventor: Aws S.M. Salim, Department of Surgery, Royal Infirmary, Perth, PH1 1NX, Scotland

[21] Appl. No.: 150,896

[22] Filed: Feb. 1, 1988

[51] Int. Cl.$^5$ .................. A61K 31/195; A61K 31/52
[52] U.S. Cl. ..................... 514/264; 514/307; 514/537; 514/560; 514/558; 514/562; 514/927
[58] Field of Search ............... 514/562, 927, 307, 537, 514/264, 558, 560

[56] References Cited

U.S. PATENT DOCUMENTS 4,029,773  6/1977  Beigler et al. ................ 514/53

FOREIGN PATENT DOCUMENTS 454077    6/1966  Japan ........................... 514/53
1177511   1/1970  United Kingdom .
1197083   7/1970  United Kingdom .
1256235  12/1971  United Kingdom .
1600639  10/1981  United Kingdom .

OTHER PUBLICATIONS

Petrikas, Chem. Abs. 86:183121h from Stomatologiya (Moscow), (1976), 55 (6), 26–9.
Ownby, et al., Chem. Abs., 83:158823 u from J. Clin. Pharmacol. (1975), 15, (5–6), pp. 419–426.
Pharmaceutical Codex, p. 740.

Primary Examiner—Frederick E. Waddell
Attorney, Agent, or Firm—Stephen G. Rudisill

[57] ABSTRACT

The present invention relates to a combination for use in improving the condition of skin and mucosa which combination comprises an S-methyl substituted ternary sulphonium derivative of methionine and cysteine. The present invention also extends to methods of treatment and prophylaxis of stress, gastric and peptic ulcers and deterioration of skin.

18 Claims, No Drawings

SYNERGISTIC COMBINATIONS

The present invention relates to synergistic combinations suitable for use in the improvement of skin and mucosal condition.

Although there is an extensive range of products available in the cosmetic market which allegedly improve skin condition these generally comprise merely barrier and/ or moisturising creams which do little more than attempt to control oil and/or water balance in the skin either by creating a barrier to transfer across the skin or by attempting to restore excessive loss from the skin. Thus such products do little if anything to improve the functioning of the skin - especially in relation to resistance to and/or recovery from injury and/or degeneration. There is also a substantial demand for safe and effective treatment and/or protection against gastric or gastroduodenal ulceration.

It is an object of the present invention to avoid or minimize one or more of the above disadvantages.

Thus the present invention provides a combination for use in improving the condition of skin and mucosa which combination comprises an S-methyl substituted ternary sulphonium derivative of methionine and cysteine.

The components of the combinations of the invention may be used in a wide range of different proportions relative to each other. In general though they are used in the range of from 0.1 to 10, preferably 0.3 to 3, parts by weight of the methionine derivative to one part by weight of cysteine though in the case of gastro-intestinal (G.I.) treatments the ratio is preferably from 5 to 1 parts of methionine derivative per 1 part of cysteine.

It will be noted that at least some of the above-mentioned compounds have one or more optically active centers, in particular in the case of the amino acids at the amino - and carboxyl - substituted carbon. For the avoidance of doubt therefore it is observed that the present invention extends to both individual isomers such as D- and L- isomers and enantiomers, and, in the case where two or more optically active centres are present, diastereoisomers, as well as mixtures of isomers including racemic DL mixtures.

Whilst not restricting the scope of the invention in any way, it is believed by the inventor that the effectiveness of the agents of the invention is due at least in part to their ability to scavenge free radicals to a greater or lesser extent and hence prevent or reduce damage to skin and mucosa caused by these.

In accordance with the present invention the application of combinations of the invention to skin and G.I. mucosa has been found to improve condition in one or more ways including improved healing of wounds and ulcers, and protection against non-mechanical injury e.g. from injurious chemical materials, stress- induced ulceration, and degeneration from other causes, including ageing. The improved condition provided by the combinations can also include maintenance of vitality and improved skin graft taking in the case of both attached or free and partial or full thickness grafts.

Advantageously the agents of the invention are used in combination with a xanthine, preferably one selected from theophylline, theobromine, aminophylline, ephidrine and caffeine, most preferably caffeine. In this case there is obtained an enhanced activity whereby the skin or mucosal condition is further improved to the extent that dermatitis, allergic or inflammatory conditions can be arrested and even reduced.

Advantageously there is also included a vasodilator such as for example menthol in order to further increase the effectiveness of the combinations.

Advantageously also there may be included an anti-ischaemic substance and in particular papaverine, and/or an anti-cholinergic and/or vagal nerve blocking substance, especially one or more compounds selected from propoxycaine and amethocaine.

In a further aspect the present invention provides a combination of the invention in intimate admixture with a physiologically acceptable carrier therefor for use in improving skin condition.

In another aspect the present invention provides a topical formulation comprising an agent of the invention in intimate admixture with a pharmaceutically acceptable vehicle therefor. The vehicle should be 'acceptable' in the sense of being generally non-deleterious to the skin of the subject being treated and compatible with the other ingredients of the formulation. It will of course be appreciated that certain individuals have significantly more sensitive skins than the average and that in these special cases alternative vehicles to those normally used may need to be tried.

Suitable vehicles are well known in the art being noted for example in such standard works as the British Pharmacopoeia and the British National Formulary and include ointment bases and cream bases as well as lotions, pastes, jellies, sprays, aerosols and bath oils. Ointments and creams may contain oleaginous absorption colloidal clays, thickening agents such as gum tragacanth or sodium alginate and other pharmaceutically acceptable accessory ingredients such as humectants, preservatives, buffers and antioxidants which have utility in such formulations.

Particularly advantageous effects have been found when certain of the agents of the invention are used together. In particular, particularly advantageous compositions, formulations and treatments of the invention contain a said methionine derivative in combination with cysteine.

In general, cream formulations are preferred as being most acceptable to the majority of users. A particularly convenient base is one utilizing cetamocrogol, comprising for example 30% w/v cetomacrogol emulsifying ointment (30% w/v cetomacrogol emulsifying wax, 20% w/v liquid paraffin wax, 50% white soft paraffin) in freshly boiled and cooled Purified water with for example 0.1% w/v chlorocresol or 0.08% w/v propyl hydroxybenzoate, 0.15% w/v methyl hydroxybenzoate and 1.5% w/v benzyl alcohol.

In general the topical formulations of the invention contain at least 0.5% w/w of a combination of the invention, preferably from 1 to 30% w/w, and most preferably from 2 to 10% e.g. 5% w/w. Where caffeine is included this is generally used in an amount of from 1 to 30% w/w.

The present invention also provides a process for producing a pharmaceutical formulation of the invention comprising bringing into intimate association a combination of the invention and a pharmaceutically acceptable vehicle therefor.

Combinations of the invention may be administered to human beings to improve skin condition and the present invention accordingly extends to a method of improving the condition of skin comprising administration of an effective dosage of an agent of the invention to the skin of a subject. As used herein an "effective dosage" means a quantity of an agent of the invention sufficient to improve the condition of skin or prevent injury to the skin by physiologically acting substances.

Where skin is being treated the agent of the invention will normally be applied in the form of a topical formulation of the invention at least once a day, preferably 2 or 3 times a day. The formulation is generally spread over the area to be treated and gently rubbed in.

In a further aspect the present invention provides a combination of the invention in intimate admixture with a physiologically acceptable carrier therefor for use in improving the condition of gastrointestinal mucosa.

In another aspect the present invention provides a gastroduodenal formulation comprising a combination of the invention in intimate admixture with a pharmaceutically acceptable vehicle therefor. The vehicle should be 'acceptable' in the sense of being generally non-deleterious to the gastroduodenal mucosa of the subject being treated and compatible with the other ingredients of the formulation.

For oral administration the combination of the invention and any accompanying material may be presented as a draught in water or in a syrup, in capsules, cachets, boluses or tablets, as an aqueous or oleaginous solution or suspension or in suspension in a syrup, such suspensions optionally including suspending agents or as an oil-in-water or water-in-oil emulsion. Where desirable or necessary flavouring, sweetening, preserving, thickening or emulsifying agents may be included in the formulation. Tablets may contain combinations of the invention and any accompanying material as a powder or granules optionally mixed with binders, lubricants, inert diluents or surface-active or dispersing agents.

For administration orally in liquid form or parenterally the combination of the invention is preferably presented in solution or suspension or emulsion at a concentration of from 5 to 25 more preferably 10 to 12% w/v in unit multi-dose form. When presented in unit dose form each unit dose preferably contains from 200 to 1200 mg of the combination of the invention, preferably from 400 to 600 mg.

In general for the purposes of treating gastro-intestinal mucosa the combination of the invention is administered at a dosage rate of from 20 to 100 mg/kg of subject bodyweight per day, preferably from 30 to 40 mg/kg/day. The dosage may be administered in one or more doses per day and preferably is administered at intervals of from 2 to 6 hours, most preferably every 4 hours. Advantageously the combination of the invention is administered in a slow release or sustained release vehicle, various suitable vehicles of this type being known in the art.

Where papaverine is included this is generally used at a dosage rate of the order of 1 mg/kg/day.

The present invention also provides a process for producing a pharmaceutical formulation of the invention comprising bringing into intimate association a combination of the invention and a pharmaceutically acceptable vehicle therefor.

Combinations of the invention may be administered to human beings to improve gastroduodenal or intestinal mucosal condition and the present invention accordingly extends to a method of improving the condition of gastroduodenal or intestinal mucosa comprising administration of an effective dosage of a combination of the invention to the gastric mucosa.

Further preferred features and advantages of the invention will appear from the following detailed examples given by way of illustration only.

EXAMPLE 1

Preparation of cream for treating skin

A topical cream having the following composition was prepared by the method described hereinbelow.

| | |
|---|---|
| DL-Methylmethionine sulphonium chloride (MMSC) | 2 g |
| L-Cysteine hydrochloride | 2 g |
| Cetomacrogol 'A' (B.P.) | add to 100 g |

The formula is prepared in a medium of 25° C. temperature. 2 g MMSC is mixed with 2 g of the cysteine hydrochloride in a glass or stainless steel container and 96 g cetomacrogol 'A' is added and mixed for 10 minutes. After standing for 30 minutes the resulting mixture is placed into an airtight opaque glass container and stored at a temperature not exceeding 26° C. No direct light should be projected at the container during the preparation which was carried out at approximately 25° C. After preparation the formula should not be used for at least 12 hours, should not be left exposed to the air for long periods, and should not be directly exposed to the sun.

EXAMPLES 2-5

Use of Topical Cream

All trials were conducted by the double blind method using the cream of Example 1 and cetomacrogol 'A' cream (B.P.) free of any other ingredients as a control.

EXAMPLE 2

A group of males and females (n=23) having an age range 18-39 years and a history of skin irritation manifested by erythema; itching and scaling following exposure to the sun for a period of less than 3 days were treated with the formula the night before and once daily for each day of exposure to direct sunlight. In all cases exposure was for more than 3 days. Of this group 17 were completely protected against irritation of skin by sunlight (74%) versus no protection in the sex and age matched controls (n=8) which had a similar history of skin irritation following exposure to the sun.

EXAMPLE 3

Twelve males of an age range 18-23 years presented with skin itching, erythema and scaling following exposure to the sun. The once daily application of the formula induced complete symptomatic relief in 8 subjects after 24 hours of treatment and on the third day 9 subjects were free of erythema and on the sixth day all but two subjects were with no signs of erythema or scaling. Controls had no benefit from their treatment during a corresponding period.

EXAMPLE 4

Twenty females of an age range 41-57 years with obvious degenerative changes of the skin (loss of smoothness and firmness, keratosis, wrinkles) were instituted on a once daily application for six weeks then a twice weekly application for 18 months. After six weeks, 14 females had obviously smoother and firmer skin, however, no significant effect was observed as to their keratosis or wrinkles. After six months of treatment all females had smoother and firmer skin but no significant change as to keratosis or wrinkles. At the end of the treatment period no new degenerative changes of any nature were observed to develop relevant to those of pretreatment and all patients had significantly improved as to their skin smoothness and firmness. Control females (n=11, age range 51-62) of similar skin changes and period of treatment with the vehicle, had no observed benefit as to their skin condition.

This effect of the formula is practiced by those actions listed in 3.

EXAMPLE 5

Eighteen females of an age range 23-37 years using a conventional market formula to avoid skin dryness and roughness were instituted on a once daily application of the formula for six weeks as a substitute for their original cream. Twelve females (67%) expressed at the end of the six weeks complete satisfaction with the formula and preference to their original cream. A similarly matched sex and age control group (n=9) instituted for the same case on the formula vehicle for the same period resulted in two cases in complete satisfaction and preference to the original cream.

EXAMPLE 6

Acute Toxicity Studies

The toxic effect of the formula was investigated in rats and guinea pigs.

Two grams of each of methylmethionine sulfonium chloride and L-cysteine hydrochloride were dissolved in 100 ml double distilled water then 1 g of menthol crystals were added producing a colourless transparent solution. A double and triple concentrations were similarly prepared.

Six groups of ten male and female Sprague-Dawley rats weighing between 180-260 g were denied solid food for 24 hours before study. Under light ether anaesthesia and by orogastric instillation into the stomach, one ml of each of the concentrations was given to a group. Similarly, one ml of each of the concentrations was injected intraperitoneally into a group.

In six other groups of ten male and female guinea pigs, similarly prepared, the same procedure was undertaken. Animals were observed for 24 hours then allowed solid food and observed for another period of six days.

There were no deaths in these groups and excitation, depression, drowsiness, vomiting or diarrhoea were not observed in any member of the treatment groups.

EXAMPLE 7

Clinical Trials

All trials were conducted by the double blind method using the cream of Example 1 and its base as a control.

1. Sixteen males (age 31-37 years) with skin excoriation and dermatitis caused by anal fistula discharge were treated by twice daily application of the formula for 10 days and a control group of males (n=11, age 28-41 years) with a similar condition were treated in the same way using the formula's base. After two days, all treatment patients were relieved of the itching and discomfort and by the seventh day after treatment commenced, 12 patients had no signs of dermatitis (erythema, oozing, scaling etc). After completion of treatment, all patients were completely relieved of all signs and symptoms of dermatitis. Control subjects were not observed to respond to their treatment and both their complaints and signs were unchanged at the end of the 10 days course.

2. Thirteen males and females (age 47-56 years) with varicose ulceration of the leg were allocated to the treatment group and seven males and females (age 39-51 years) with a similar condition were allocated to the control group.

In both groups the ulcer was initially dried with twice daily application of magnesium sulphate powder with conventional dressing, bed rest and elevation of the ulcerated leg. After 3 days, only the powder was substituted for a twice daily application of the formula or its base for 8 weeks. During the first two weeks of treatment, patients were confined to bed and the ulcerated leg elevated. Then patients were allowed out of bed and leg elevation was limited to their sleeping hours.

After four weeks of treatment, all thirteen patients using the formula had a significant reduction in the size of their ulceration and in every case the ulcer demonstrated active healing signs. After 8 weeks, ten patients had complete healing and three patients were still with ulceration. In the control group, one ulcer healed, two showed active signs of healing and the rest of ulcers were unaffected.

3. Following tangential excision of burns and grafting with partial thickness skin, 21 males and females (age 9-37 years) had a liberal amount of the formula applied to the graft before dressing and 20 males and females (age 13-41 years) had a similar application of the formula base.

On the fifth day after grafting, all patients in the treatment group had complete graft taking, whereas in the control group there were three graft failure and 4 cases of incomplete graft taking.

4. Following a third and fourth degree burn of the limbs and body, 11 males and females (age 9-26 years) received twice daily application of the formula to their burns for 21 days whereas 10 males and females (age 6-19 years) were similarly treated with the formula base.

Treatment with the formula resulted in significantly better burn healing in terms of discolouration, erythema, vascular granulation. It was also observed that local discomfort was by far less in those patients having treatment with the formula than in those receiving its base.

5. After skin closure, 27 males (age 26-53 years) with an upper midline or paramedian laparotomy incision for elective surgery had a liberal amount of the formula applied to their wounds before dressing. Controls were 10 males (age 31-42 years) with similar laparotomy incisions receiving the formula's base.

All operations were performed by the same surgeon using the same wound closing procedure. Stitches were removed on the 7th and 8th post-operative day. Wound complications were not observed in members of either group and each group had a second application of their own treatment and wounds were left open. Inspection of wounds on the fourth post-operative week demonstrated that the formula resulted in cosmetically better healing with apparently less scarring beyond the wound margins than in controls.

What is claimed is:

1. A combination suitable for use in improving the condition of skin and mucosa which combination comprises an S-methyl substituted ternary sulphonium derivative of methionine and cysteine wherein said cysteine and methionine derivative are present in a relative ratio of from 1:10 to 10:1, by weight.

2. A combination as claimed in claim 1 wherein said cysteine and methionine derivative are present in a relative ration of from 3:10 to 1:3, by weight.

3. A combination as claimed in claim 1 wherein said methionine derivative comprises methyl methionine sulphonium chloride.

4. A combination as claimed in claim 1 which includes at least one of an anti-ischaemic substance, an anti-cholinergic substance, and a vagal nerve blocking substance.

5. A combination as claimed in claim 4 which includes at least one of papaverine, propoxycaine and amethocaine.

6. A combination as claimed in claim 1 which includes a xanthine selected from theophylline, theobromine, aminophylline, ephidrine, and caffeine.

7. A combination as claimed in claim 1 which includes a vasodilator.

8. A combination as claimed in claim 7 wherein said vasodilator comprises menthol.

9. A combination as claimed in claim 1 which includes castor oil.

10. A pharmaceutical composition suitable for use in improving the condition of skin and mucosa comprising, in combination cysteine and a S-methyl substituted ternary sulphonium derivative of methionine in intimate admixture with a physiologically acceptable carrier therefor.

11. A composition as claimed in claim 10 which composition is in the form of a topical formulation.

12. A composition as claimed in claim 10 which composition is in the form of an orally ingestible formulation.

13. A composition as claimed in claim 12 which is in the unit dosage form.

14. A method of treatment or polylaxis of at least one of stress, gastric and peptic ulcers comprising the administration of a therapeutically or prophylactically effective dosage of a combination comprising cysteine and a S-methyl substituted ternary sulphonium derivative of methionine in intimate admixture with a physiologically acceptable carrier therefor, to said mammal wherein said cysteine and methionine derivative are administered in a relative ratio of from 1:1 to 1:5, by weight.

15. A method as claimed in claim 14 wherein said combination is administered orally.

16. A method as claimed in claim 15 wherein said combination is administered in unit dosage form.

17. A method as claimed in claim 14 wherein said combination is administered with said cysteine and methionine derivative in a relative ratio of from 1:1 to 1:5 parts by weight.

18. A method of improving the condition of mucosa in a mammal comprising the administration of an effective dosage of cysteine in combination with an S-methyl substituted ternary sulphonium derivative of methionine wherein said cysteine and methionine derivative are administered in a relative ratio of from 1:10 to 10:1, by weight.

* * * * *